US00PP15212P2

(12) United States Plant Patent
Guillen

(10) Patent No.: US PP15,212 P2
(45) Date of Patent: Oct. 12, 2004

(54) ***IMPATIENS* PLANT NAMED 'BALPIXPICO'**

(50) Latin Name: *Impatiens walleriana*
Varietal Denomination: Balpixpico

(75) Inventor: Mario Guillen, Cartago (CR)

(73) Assignee: Ball FloraPlant, a division Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/113,591

(22) Filed: Apr. 1, 2002

(51) Int. Cl.[7] ..... A01H 5/00
(52) U.S. Cl. ..... Plt./317
(58) Field of Search ..... Plt./317

*Primary Examiner*—Kent Bell
(74) *Attorney, Agent, or Firm*—Wood, Phillips, Katz, Clark & Mortimer

(57) ABSTRACT

A new and distinct *Impatiens* plant named 'Balpixpico', characterized by its small pink and white bicolor flowers, compact growth habit and dark green leaves.

1 Drawing Sheet

Latin name of the genus and species of plant claimed: *Impatiens walleriana.*
Variety denomination: 'Balpixpico'.

BACKGROUND OF THE INVENTION

The present invention comprises a new and distinct *Impatiens* plant, botanically known as *Impatiens walleriana* and hereinafter referred to by the cultivar name 'Balpixpico'.

'Balpixpico' is a product of a planned breeding program with the objective of developing *Impatiens* cultivars with small flowers and compact growth habits.

The female or seed parent of 'Balpixpico' was an unnamed *Impatiens* plant. The male or pollen parent of 'Balpixpico' was a mix of pollen from plants of the seed *Impatiens* series SUPER ELFIN®. The new cultivar was discovered and selected as a single flowering plant within the progeny of the above stated cross during October 1999 in a controlled environment at Elburn, Ill. The new cultivar was initially designated 'BFP-518'.

Asexual reproduction of the new cultivar has been carried out at West Chicago, Ill. by terminal tip cuttings and has demonstrated that the unique characteristics of the new cultivar as herein described are firmly fixed and retained through successive generations of such asexual propagation.

SUMMARY OF THE INVENTION

It was found that the cultivar of the present invention:

(a) exhibits small pink and white bicolor flowers;

(b) forms dark green foliage;

(c) exhibits a good basal branching character; and (d) exhibits a compact growth habit.

Plants of the new cultivar differ from plants of the female parent plant primarily in flower color. The new cultivar of the present invention can be compared to 'Fify Violet' (U.S. Plant Pat. No. 11,577). However, in side-by-side comparisons, plants of the new cultivar are more vigorous and have flowers that are lighter in color than 'Fify Violet'.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown for 12 weeks in a greenhouse at West Chicago, Ill.

DETAILED BOTANICAL DESCRIPTION

The cultivar 'Balpixpico' has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Feb. 12, 2002. The readings were taken between 2:00 and 3:00 p.m. under natural daylight conditions.

Plants used for the following descriptions and measurements were grown in 10 cm pots for 12 weeks from rooted cuttings. The plants were produced from cuttings taken from stock plants and grown in a double polycarbonate covered greenhouse under conditions comparable to those used in commercial practice. A soilless growth medium was utilized while temperatures of approximately 68° to 75° F. (20° to 24° C.) during the day and approximately 55° to 65° F. (13° to 18° C.) during the night and light levels of 4,000 to 6,000 footcandles were maintained.

Classification:
- *Botanical.*—*Impatiens walleriana* cultivar 'Balpixpico'.

Parentage:
- *Female parent.*—Unnamed *Impatiens* plant.
- *Male parent.*—Mix of pollen from the SUPER ELFIN® series of *Impatiens.*

Propagation:
- *Type cutting.*—Terminal tip.
- *Time to initiate roots.*—Approximately 7 to 10 days.
- *Time to develop roots.*—Approximately 21 to 30 days.
- *Root description.*—Fibrous, branching.

Plant description:
- *Crop time.*—Approximately 4 to 6 weeks are required to produce a finished plant from rooted cuttings.
- *Habit of growth.*—Compact with good basal branching. Pinching is not required.

*Form.*—Upright and mounded.

*Plant height from soil to top of plant plane.*—A mature plant, 12 weeks after the planting of a rooted cutting, commonly measures approximately 14.8 cm.

*Plant spread.*—Approximately 26.5 cm.

*Lateral branches.*—An average of 8 branches per plant, approximately 7 cm in length and 4 mm in diameter, glabrous and 146C with streaks of 59A. Internode length at the middle of the branch is approximately 3 mm.

*Foliage.*—Arrangement is alternate. Leaves are single, ovate with crenate, ciliate margin, acuminate apex, attenuate base and are at an acute angle to the stem. Upper and lower surfaces are glabrous. Leaf length is approximately 2.9 cm and width is approximately 1.6 cm. The upper surface of mature foliage is 147A and the lower surface is closest to 147B with blotches of 183D. Both upper and lower surfaces have pinnate venation. Venation of upper surface is 144C and the venation of the lower surface is 144B. The petiole length is approximately 1.9 cm, the diameter is approximately 2 mm and the color is closest to 144D with streaks of 59B.

Flowering description:

*Flowering habit.*—Freely flowering.

*Natural flowering season.*—Year round in greenhouse environment and from spring through fall in outdoor garden.

Flower description:

*Type.*—Single and persistent.

*Size.*—Diameter: Approximately 2.6 cm. Depth: Approximately 0.5 cm.

*Quantity per plant.*—Approximately 40 fully open flowers at any one time.

*Fragrance.*—None.

*Lastingness of the bloom.*—Approximately 4 to 7 days.

*Aspect.*—Flat.

*Corolla.*—Five petals with entire undulate margin. Upper petal has cuspidate apex, lateral petals have rounded apex and lower petals have emarginate apex. Upper petal has flat base. Lateral and lower petals are fused at the base. All petals have a smooth texture. Upper petal length is approximately 1.1 cm and the width at the widest point is 1.5 cm. Lateral and lower petal length is approximately 1.5 cm and the width at the widest point is approximately 1 cm. Petals vary in color. The upper surface of some petals is entirely 155D, some are 73A at the margin with the color gradually fading to 73C toward the base and 61A at the base and other petals are 73A at margin fading gradually through 73C toward the base and 61A at the base but also have various amounts of 155D. The color of the lower surface of the petals varies from 155D to 72B at the margin gradually fading through 73C in the center to 73D at the base. The petal color fades to 81C with age.

*Peduncle.*—Glabrous, at an acute angle to the stem, approximately 1.3 cm in length and 1 mm in diameter. The peduncle color is 144C with streaks of 59A.

*Flower bud.*—Ovate, approximately 9 mm in length and 5 mm in diameter at first color. The bud color is 73B.

*Sepals.*—Quantity: Four per flower. The upper sepal is fused to the lower surface of the upper petal. The upper sepal length: approximately 7 mm. The upper sepal width: approximately 3 mm. The upper sepal color: 144C with a midrib of 144B. The lateral sepal length: approximately 3 mm. The lateral sepal width: approximately 1 mm. The lateral sepal color: 146D. The lower sepal is modified to form nectary spur.

*Spur.*—Shape: Sharply curved. Length: approximately 2.5 cm. Diameter at flower: 2 mm. Diameter at tip: 0.6 mm. Color: 154D.

*Reproductive organs.*—Five stamens, 3 mm in length. Anthers are fused around the pistil and the color is 70A. Pollen is scarce and is 72A. Pistil number: one per flower. Pistil length: 3 mm. Style length is <1 mm and the color is 70A. Stigma length is <1 mm and the color is 71A. The ovary is 2 mm in length and is 144A in color.

Seed production: Seed production has not been observed.

Disease resistance: Resistance to pathogens has not been observed.

Hardiness zone: 'Balpixpico' is hardy in zones nine (9) and above.

I claim:

1. A new and distinct cultivar of *Impatiens* plant named 'Balpixpico' substantially as herein shown and described, which:

(a) exhibits small pink and white bicolor flowers;

(b) dark green foliage;

(c) a compact growth habit; and (d) a good basal branching character.

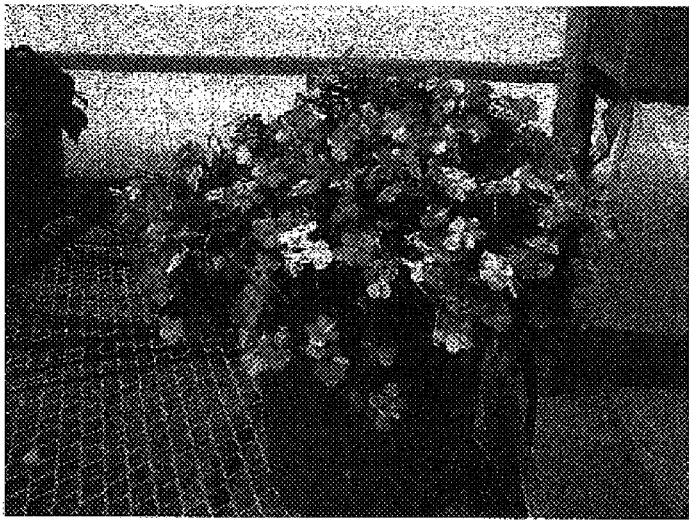

* * * * *